US007365221B2

(12) United States Patent
Allaway et al.

(10) Patent No.: US 7,365,221 B2
(45) Date of Patent: Apr. 29, 2008

(54) MONOACYLATED BETULIN AND DIHYDROBETULIN DERIVATIVES, PREPARATION THEREOF AND USE THEREOF

(75) Inventors: Graham P. Allaway, Darnestown, MD (US); Carl T. Wild, Gaithersburg, MD (US); Yoshiki Kashiwada, Niigata (JP); Kuo-Hsiung Lee, Chapel Hill, NC (US)

(73) Assignees: Panacos Pharmaceuticals, Inc., Gaithersburg, MD (US); The University of North Carolina at Chapel Hill, Chapel Hill, NC (US); Niigata University of Pharmacy and Applied Life Sciences, Niigata (JP)

( * ) Notice: Subject to any disclaimer, the term of this patent is extended or adjusted under 35 U.S.C. 154(b) by 432 days.

(21) Appl. No.: 10/870,555

(22) Filed: Jun. 18, 2004

(65) Prior Publication Data

US 2005/0020548 A1 Jan. 27, 2005

Related U.S. Application Data

(63) Continuation-in-part of application No. 10/670,797, filed on Sep. 26, 2003, now abandoned.

(60) Provisional application No. 60/413,451, filed on Sep. 26, 2002.

(51) Int. Cl.
C07C 69/74 (2006.01)
(52) U.S. Cl. .................. 560/116; 514/169; 552/511
(58) Field of Classification Search ................ 560/116; 514/169; 552/511
See application file for complete search history.

(56) References Cited

U.S. PATENT DOCUMENTS

| 5,679,828 A | 10/1997 | Lee et al. |
| 6,172,110 B1 | 1/2001 | Lee et al. |

FOREIGN PATENT DOCUMENTS

| WO | WO 96/39033 A1 | 12/1996 |
| WO | WO 00/59492 A2 | 10/2000 |
| WO | WO 01/59457 A2 | 8/2001 |
| WO | WO 02/16395 A1 | 2/2002 |
| WO | WO 02/26761 A1 | 4/2002 |
| WO | WO 02/26762 A1 | 4/2002 |

OTHER PUBLICATIONS

Pokrovskii, A. G.; Plyasunvoa, O. A.; Il'icheva, T. N.; Borisova, O. A.; Fedyuk, N. V.; Petrenko, N. I.; Petukhova, V. Z.; Shul'ts, E. E.; Tolstikov, G. A. Synthesis of derivatives of plant triterpenes and study of their antiviral and immunostimulating activity. Khimiya v Interesakh Ustoichivogo Razvitiya (2001), 9(3), 485-491.*

Pasich, Jan. Triterpenoid emulsifiers of plant origin. V. Emulsifying properties of betulin and certain of its esters. Farm. Polska (1965), 21(17-18), 661-5.*

Fujioka, T., and Kashiwada, Y., "Anti-AIDS Agents. 11. Betulinic Acid and Platanic Acid as Anti-HIV Principles from *Syzigium claviflorum*, and the Anti-HIV Activity of Structurally Related Triterpenoids," *J. Nat. Prod.* 57:243-247, American Chemical Society and American Society of Pharmacognosy (1994).

Hashimoto, F., et al., "Anti-AIDS Agents-XXVII. Synthesis and Anti-HIV Activity of Betulinic Acid and Dihydrobetulinic Acid Derivatives," *Bioorg. Med. Chem.* 5:2133-2143, Elsevier Science, Ltd. (1997).

Kanamoto, T., et al., "Anti-Human Immunodeficiency Virus Activity of YK-FH312 (a Betulinic Acid Derivative), a Novel Compound Blocking Viral Maturation," *Antimicrobial Agents Chemother.* 45:1225-1230, American Society for Microbiology (Apr. 2001).

Kashiwada, Y., et al., "Betulinic Acid and Dihydrobetulinic Acid Derivatives as Potent Anti-HIV Agents," *J. Med. Chem.* 39:1016-1017, American Chemical Society (1996).

Kashiwada, Y., et al., "Anti-AIDS Agents. 30. Anti-HIV Activity of Oleanolic Acid, Pomolic Acid, and Structurally Related Triterpenoids," *J. Nat. Prod.* 61:1090-1095, American Chemical Society and American Society of Pharmacognosy (1998).

Kashiwada, Y., et al., "Synthesis and Anti-HIV Activity of 3-Alkylamido-3-deoxy-betulinic Acid Derivatives," *Chem. Pharm. Bull.* 48:1387-1390, Pharmaceutical Society of Japan (2000).

Kashiwada, Y., et al., "Anti-AIDS Agents 38. Anti-HIV Activity of 3-*O*-Acyl Ursolic Acid Derivatives," *J. Nat. Prod.* 63:1619-1622, American Chemical Society and American Society of Pharmacognosy (2000).

Ma, C., et al., "Inhibitory Effects of Ursolic Acid Derivatives from *Cynomorium songaricum*, and Related Triterpenes on Human Immunodeficiency Viral Protease," *Phytother. Res. (Supplement 1, 2nd Intl' Symposium on Natural Drugs)* 12:S138-S142, John Wiley & Sons, Ltd. (1998).

Ma, C., et al., "Inhibitory Effects of Constituents from *Cynomorium songaricum* and Related Triterpene Derivatives on HIV-1 Protease," *Chem. Pharm. Bull.* 47:141-145, Pharmaceutical Society of Japan (1999).

Neamati, N., "A Small-molecule Antagonist of Virion Assembly," *Expert Opin. Investig. Drugs* 10:1767-1770, Ashley Publications, Ltd. (Sep. 2001).

Pokrovskii, A.G., et al., "Synthesis of Derivatives of Plant Triterpenes and Study of Their Antiviral and Immunostimulating Activity," *Khimiya v Interesakh Ustoichivogo Razvitiya* 9:485-491, Siberian Branch of the Russian Academy of Sciences (2001).

(Continued)

*Primary Examiner*—Yvonne Eyer
*Assistant Examiner*—Sudhakar Katakam
(74) *Attorney, Agent, or Firm*—Sterne, Kessler, Goldstein & Fox P.L.L.C.

(57) ABSTRACT

Betulin and dihydrobetulin acyl derivatives according to the present invention have been found to have potent anti-HIV activity. The compounds of the present invention have Formula I as described herein, or pharmaceutically acceptable salts thereof; wherein $R_1$ is a $C_2$-$C_{20}$ substituted or unsubstituted carboxyacyl or ester thereof; $R_2$ is hydrogen, halogen, hydroxyl or —$OR_3$, $R_3$ is $C_2$-$C_{20}$ substituted or unsubstituted carboxyacyl; and $R_4$ is hydrogen or $C(C_6H_5)_3$; wherein the dashed line represents an optional double bond between C20 and C29.

23 Claims, No Drawings

OTHER PUBLICATIONS

Sun, I-C., et al., "Anti-AIDS Agents. 34. Synthesis and Structure-Activity Relationships of Betulin Derivatives as Anti-HIV Agents," *J. Med. Chem.* 41:4648-4657, American Chemical Society (1998).

Sun, I-C., et al., "Anti-AIDS Agents. 32. Synthesis and Anti-HIV Activity of Betulin Derivatives," *Bioorg. Med. Chem. Lett.* 8:1267-1272, Elsevier Science, Ltd. (1998).

STNEasy, Accession No. 2001:541179, CAPLUS, ACS on STN (2003), English language abstract for Pokrovskii, A.G., et al., "Synthesis of Derivatives of Plant Triterpenes and Study of Their Antiviral and Immunostimulating Activity," *Khimiya v Interesakh Ustoichivogo Razvitiya* 9:485-491 (2001).

\* cited by examiner

MONOACYLATED BETULIN AND DIHYDROBETULIN DERIVATIVES, PREPARATION THEREOF AND USE THEREOF

This application is a Continuation-in-Part of U.S. Non-Provisional application Ser. No. 10/670,797, filed Sep. 26, 2003, now abandoned which claims the benefit of U.S. Provisional Application No. 60/413,451, filed Sep. 26, 2002, the entirety of which both are fully incorporated by reference herein.

BACKGROUND OF THE INVENTION

1. Field of the Invention

The present invention relates to novel synthetic derivatives of betulin and dihydrobetulin and the use of such derivatives as pharmaceuticals.

2. Related Art

Retroviruses are small, single-stranded positive-sense RNA viruses. A retroviral particle comprises two identical single-stranded positive sense RNA molecules. Their genome contains, among other things, the sequence of the RNA-dependent DNA polymerase, also known as reverse transcriptase. Many molecules of reverse transcriptase are found in close association with the genomic RNA in the mature viral particles. Upon entering a cell, this reverse transcriptase produces a double-stranded DNA copy of the viral genome, which is then inserted into the chromatin of a host cell. Once inserted, the viral sequence is called a provirus. Retroviral integration is directly dependent upon viral proteins. Linear viral DNA termini (the LTRs) are the immediate precursors to the integrated proviral DNA. There is a characteristic duplication of short stretches of the host's DNA at the site of integration.

Progeny viral genomes and mRNAs are transcribed from the inserted proviral sequence by host cell RNA polymerase in response to transcriptional, regulatory signals in the terminal regions of the proviral sequence, the long terminal repeats, or LTRs. The host cell's protein production machinery is used to produce viral proteins, many of which are inactive until processed by virally encoded proteases. Typically, progeny viral particles bud from the cell surface in a non-lytic manner. Retroviral infection does not necessarily interfere with the normal life cycle of an infected cell or organism. However, neither is it always benign with respect to the host organism. While most classes of DNA viruses can be implicated in tumorigenesis, retroviruses are the only taxonomic group of RNA viruses that are oncogenic. Various retroviruses, such as the Human Immunodeficiency Virus (HIV), which is the etiological agent responsible for acquired immune deficiency syndrome (AIDS) in humans, are also responsible for several very unusual diseases of the immune system of higher animals.

Human Immunodeficiency Virus (HIV) is a member of the lentiviruses, a subfamily of retroviruses. HIV infects and invades cells of the immune system; it breaks down the body's immune system and renders the patient susceptible to opportunistic infections and neoplasms. The immune defect appears to be progressive and irreversible, with a high mortality rate that approaches 100% over several years.

HIV-1 is trophic and cytopathic for T4 lymphocytes, cells of the immune system which express the cell surface differentiation antigen CD4, also known as OKT4, T4 and leu3. The viral tropism is due to the interactions between the viral envelope glycoprotein, gp120, and the cell-surface CD4 molecules (Dalgleish et al., *Nature* 312:763-767 (1984)). These interactions not only mediate the infection of susceptible cells by HIV, but are also responsible for the virus-induced fusion of infected and uninfected T cells. This cell fusion results in the formation of giant multinucleated syncytia, cell death, and progressive depletion of CD4 cells in HIV-infected patients. These events result in HIV-induced immunosuppression and its subsequent sequelae, opportunistic infections and neoplasms.

In addition to CD4+ T cells, the host range of HIV includes cells of the mononuclear phagocytic lineage (Dalgleish et al., supra), including blood monocytes, tissue macrophages, Langerhans cells of the skin and dendritic reticulum cells within lymph nodes. HIV is also neurotropic, capable of infecting monocytes and macrophages in the central nervous system causing severe neurologic damage. Macrophage/monocytes are a major reservoir of HIV. They can interact and fuse with CD4-bearing T cells, causing T cell depletion and thus contributing to the pathogenesis of AIDS.

Considerable progress has been made in the development of drugs for HIV-1 therapy during the past few years. Therapeutic agents for HIV can include, but not are not limited to, at least one of AZT, 3TC, ddC, d4T, ddI, tenofovir, abacavir, nevirapine, delavirdine, emtricitabine, efavirenz, saquinavir, ritonavir, indinavir, nelfinavir, lopinavir, amprenavir, and atazanavir or any other antiretroviral drugs or antibodies in combination with each other, or associated with a biologically based therapeutic, such as, for example, gp41-derived peptides enfuvirtide (Fuzeon; Timeris-Roche) and T-1249 (Trimeris), or soluble CD4, antibodies to CD4, and conjugates of CD4 or anti-CD4, or as additionally presented herein. Combinations of these drugs are particularly effective and can reduce levels of viral RNA to undetectable levels in the plasma and slow the development of viral resistance, with resulting improvements in patient health and life span.

Despite these advances, there are still problems with the currently available drug regimens. Many of the drugs exhibit severe toxicities, have other side-effects (e.g., fat redistribution) or require complicated dosing schedules that reduce compliance and thereby limit efficacy. Resistant strains of HIV often appear over extended periods of time even on combination therapy. The high cost of these drugs is also a limitation to their widespread use, especially outside of developed countries.

There is still a major need for the development of additional drugs to circumvent these issues. Ideally these would target different stages in the viral life cycle, adding to the armamentarium for combination therapy, and exhibit minimal toxicity, yet have lower manufacturing costs.

Previously, betulinic acid and platanic acid were isolated as anti-HIV principles from *Syzigium claviflorum*. Betulinic acid and platanic acid exhibited inhibitory activity against HIV-1 replication in H9 lymphocyte cells with $EC_{50}$ values of 1.4 µM and 6.5 µM, respectively, and T.I. values of 9.3 and 14, respectively. Hydrogenation of betulinic acid yielded dihydrobetulinic acid, which showed slightly more potent anti-HIV activity with an $EC_{50}$ value of 0.9 and a T.I. value of 14 (Fujioka, T., et al., *J. Nat. Prod.* 57:243-247 (1994)).

Esterification of betulinic acid (1) with certain substituted acyl groups, such as 3',3'-dimethylglutaryl and 3',3'-dimethylsuccinyl groups produced derivatives having enhanced activity (Kashiwada, Y., et al., *J. Med. Chem.* 39:1016-1017 (1996)). Acylated betulinic acid and dihydrobetulinic acid derivatives that are potent anti-HIV agents are also described in U.S. Pat. No. 5,679,828.

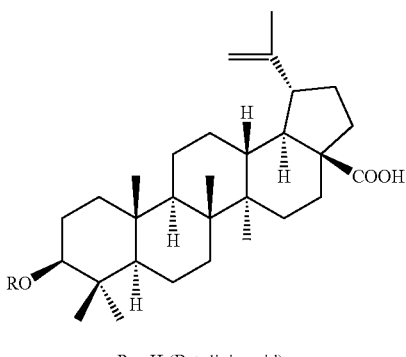

R = H (Betulinic acid)

U.S. Pat. No. 5,468,888 discloses 28-amido derivatives of lupanes that are described as having a cytoprotecting effect for HIV-infected cells.

Japanese Patent Application No. JP 01 143,832 discloses that betulin and 3,28-diesters thereof are useful in the anti-cancer field.

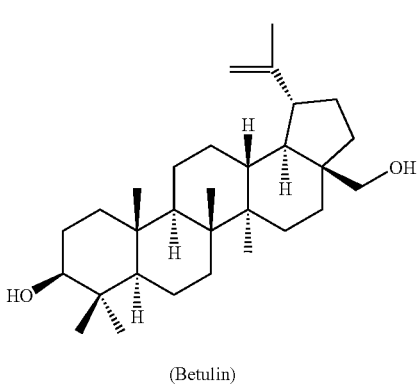

(Betulin)

U.S. Pat. No. 6,172,110 discloses betulin and dihydrobetulin derivatives found to have potent anti-HIV activity.

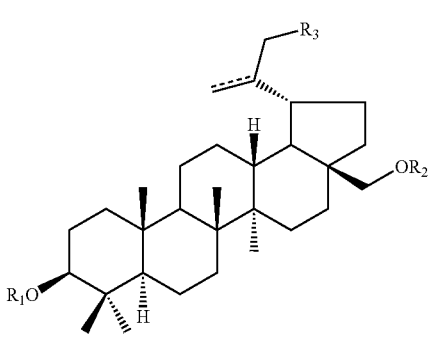

(betulin and dihydrobetulin derivatives)

Esterification of the 3 carbon of betulin with succinic acid produced a compound capable of inhibiting HIV-1 activity (Pokrovskii, A. G., et al., *Gos. Nauchnyi Tsentr Virusol. Biotekhnol. "Vector"* 9:485-491 (2001)).

U.S. Pat. No. 6,642,217 discloses the use of betulin and analogs thereof for treating fungal and yeast infections.

A need continues to exist for compounds which possess potent antiretroviral activity, especially anti-HIV activity, with improved biodistribution properties and different modes of action. Such compounds are urgently needed to add to existing anti-HIV therapies. There is also a need for safe and effective compound that can be topically applied to vaginal or other mucosa to prevent HIV infection between individuals.

SUMMARY OF THE INVENTION

A first aspect of the present invention is directed to novel compounds of Formula I:

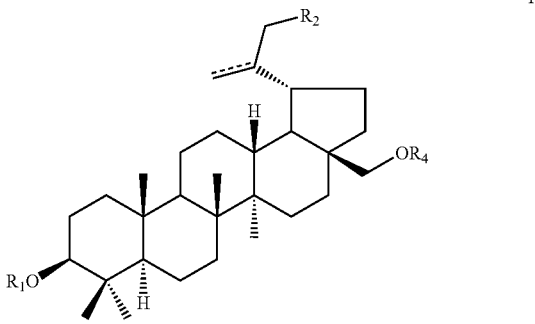

I or pharmaceutically acceptable salts thereof, wherein
$R_1$ is a $C_2$-$C_{20}$ substituted or unsubstituted carboxyacyl, or ester thereof;
$R_2$ is hydrogen, halogen, hydroxyl or —$OR_3$;
$R_3$ is $C_2$-$C_{20}$ substituted or unsubstituted carboxyacyl; and
$R_4$ is hydrogen or $C(C_6H_5)_3$;
wherein the dashed line represents an optional double bond between C20 and C29.

A second aspect of the present invention is directed to pharmaceutical compositions, comprising one or more compounds of Formula I, and a pharmaceutically acceptable carrier or diluent. One or more additional pharmaceutically active compounds can also be included in these compositions.

The compounds of Formula I are useful as anti-retroviral agents. Therefore, the present invention provides methods for inhibiting a retroviral infection in cells or tissue of an animal, comprising administering an effective retroviral inhibiting amount of a compound of Formula I. A preferred embodiment is directed to a method for treating a patient suffering from a retroviral-related pathology, comprising administering to the subject a retroviral inhibiting effective amount of a pharmaceutical composition that includes a compound of Formula I.

The 3-O-acyl betulin and dihydrobetulin derivatives of Formula I can be used in combination therapy with one or more anti-viral agents. Thus, the present invention provides a method of treating a patient suffering from a retroviral-related pathology, comprising administering to the patient a retroviral inhibiting effective amount of a compound of Formula I in combination with one or more anti-viral agents. Preferably, the anti-viral agent is approved for use for HIV-therapy in the U.S.

The present invention also provides a method of preventing transmission of HIV infection between individuals. In particular, the present invention provides a method of preventing transmission of HIV infection from an HIV infected pregnant woman to a fetus, comprising administering to the woman and/or the fetus a retroviral inhibiting effective amount of one or more compounds of Formula I during pregnancy or immediately prior to, at, or subsequent to birth.

Further, the present invention provides a method of preventing transmission of HIV infection during sexual intercourse, comprising applying a retroviral inhibiting effective amount of a topical composition including one or more compounds of Formula I to vaginal or other mucosa prior to sexual intercourse.

Furthermore, the present invention is directed to a method for making compounds of Formula I.

Additional embodiments and advantages of the invention will be set forth in part in the description as follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE PREFERRED EMBODIMENTS

The compounds of the present invention have the general Formula I:

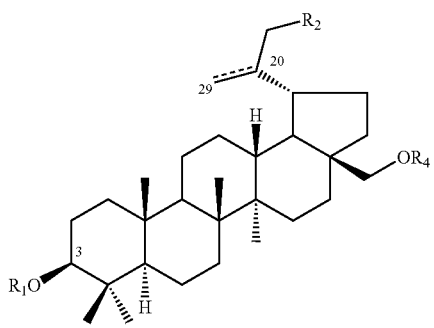

I or a pharmaceutically acceptable salt thereof; wherein $R_1$ is a $C_2$-$C_{20}$ substituted or unsubstituted carboxyacyl, or ester thereof;

$R_2$ is hydrogen, halogen, hydroxyl or —$OR_3$;

$R_3$ is $C_2$-$C_{20}$ substituted or unsubstituted carboxyacyl; and $R_4$ is hydrogen or $C(C_6H_5)_3$;

wherein the dashed line represents an optional double bond between C20 and C29; provided that $R_1$ is not succinyl, i.e.

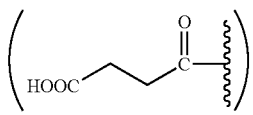

Preferred compounds of the present invention are those where $R_2$ is hydrogen. In one embodiment, the bond between C20 and C29 is a double bond. In another embodiment, the bond between C20 and C29 is a single bond.

Another group of preferred compounds are those where $R_2$ is halogen or —$OR_3$, where $R_3$ is $C_2$-$C_{20}$ substituted or unsubstituted carboxyacyl. In one embodiment, the bond between C20 and C29 is a double bond. In another embodiment, the bond between C20 and C29 is a single bond.

Even more preferred are those compounds described above wherein $R_1$ is a $C_4$-$C_{16}$ carboxyalkanoyl group that is mono- or di- substituted at the 3' carbon atom. Such a side chain has the formula:

—C(O)CH$_2$CR'R"(CH$_2$)$_b$COOH where R' and R" are each $C_1$-$C_4$ alkyl, preferably methyl or ethyl, or R' is hydrogen and R" is $C_1$-$C_4$ alkyl, or R' and R" are taken together to form a di-, tri, tetra-, penta-, hexa- or heptamethylene linkage, and b is from zero to 12, preferably zero to 4, most preferably zero or 1.

In some embodiments, $R_1$ can contain one or more double bonds.

In some embodiments, $R_1$ is an ester of $C_2$-$C_{20}$ substituted or unsubstituted carboxyacyl. Various esters may be formed via the carboxyl group of the carboxyacyl side chain. Such an $R_1$ sidechain can have the generic formula:

—C(O)(CH$_2$)$_d$CR'R"(CH$_2$)$_b$COOR$_5$ where b, R' and R" are defined as above. In some embodiments, d is from zero to 12, preferably zero to 4, more preferably zero to 1. In some embodiments, $R_5$ can be $C_1$-$C_6$ alkyl or $C_1$-$C_6$ carboxyalkyl where the alkyl group is a straight or branched chain. In some embodiments, $R_5$ can include $C_{5-7}$ cycloalkyl or arylalkyl, such as, but not limited to, benzyl. In some embodiments, $R_5$ is $C_1$-$C_4$ alkyl. In some embodiments, $R_5$ is ethyl. The esters of $R_1$ can be formed by reacting an alcohol with the carboxyl group of the carboxyacyl $R_1$ group. This carboxyacyl group can be activated by forming the acid chloride, anhydride or other reactive acid functional groups as is well known in the art. In some embodiments, the ester group is substituted with one or more hydroxyls or halogens.

Additionally preferred are those compounds described above where $R_1$ is a $C_4$-$C_{16}$ carboxyalkoxyacetyl group of the formula:

—C(O)CH$_2$O(CH$_2$)$_a$COOH, where a is from one to ten, preferably one to four, most preferably one or two.

Preferred values of $R_2$ include: hydrogen, halogen, or —$OR_3$, where $R_3$ is preferably hydrogen; —C(O)CH$_2$CR'R" (CH$_2$)$_b$COOH, where R', R" and b are as defined above; or —C(O)CH$_2$O(CH$_2$)$_a$COOH, where a is as defined above.

Useful compounds include those of Formula I, wherein:

$R_1$ is one of:

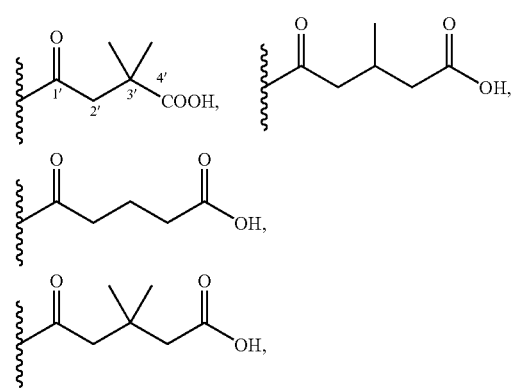

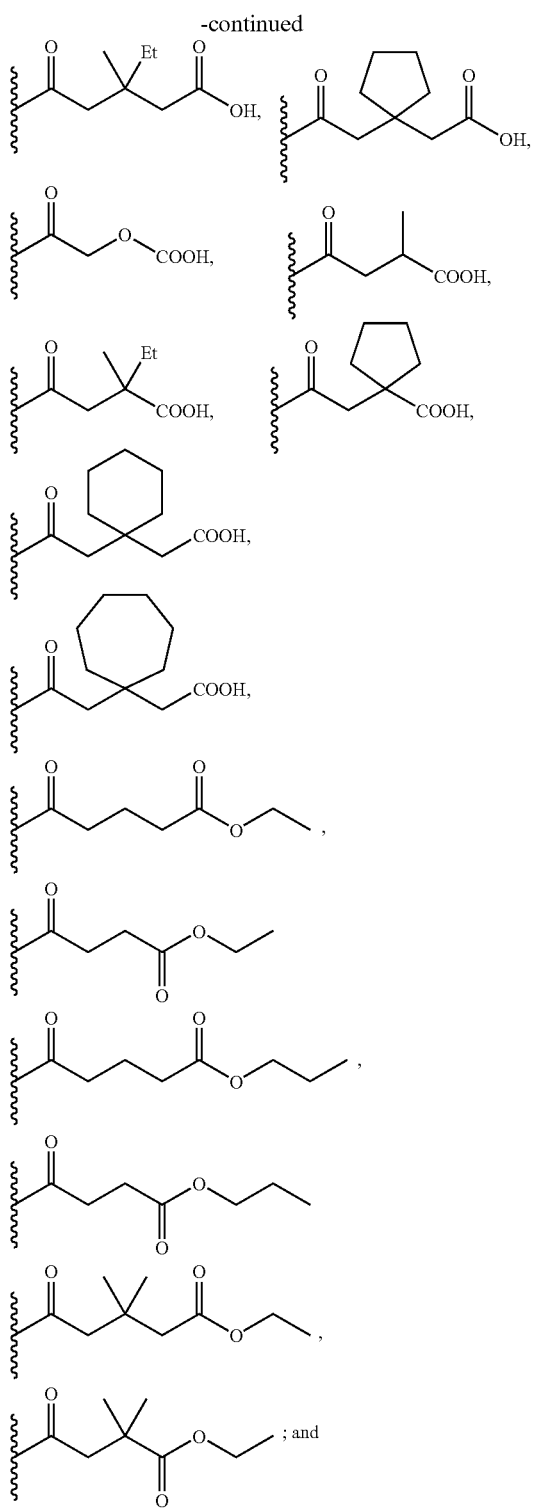
$R_2$ is hydrogen, chloro, bromo, or hydroxyl.
In some embodiments, $R_1$ is
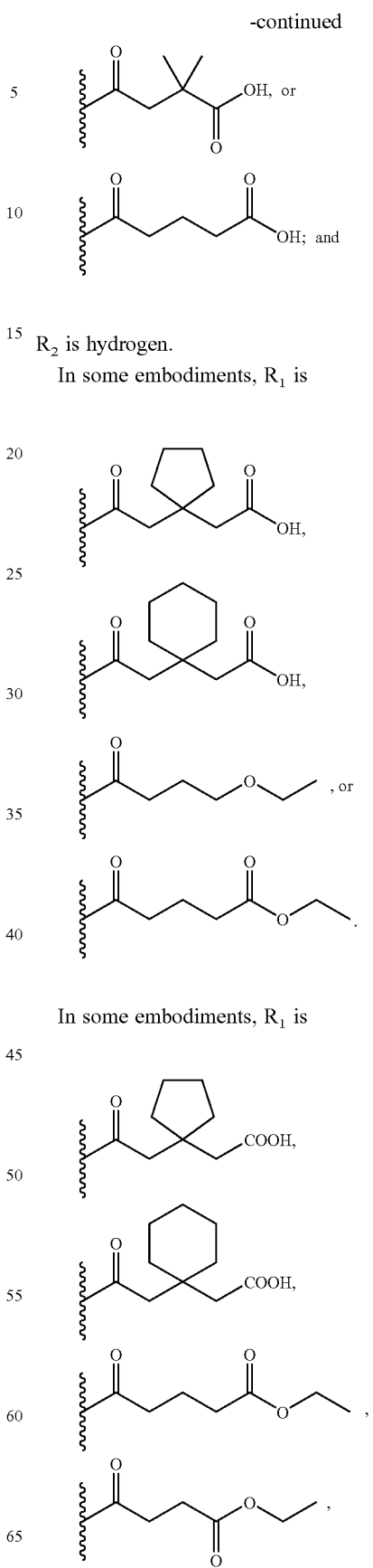
$R_2$ is hydrogen.
In some embodiments, $R_1$ is
In some embodiments, $R_1$ is

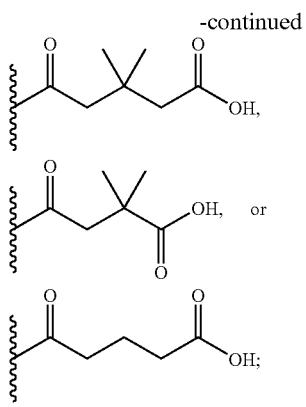

R$_2$ is H; and a double or a single bond exists between C20 and C29.

In the present invention, the sidechains R$_1$ and R$_3$ of the present invention can be substituted or unsubstituted. In some embodiments, R$_1$ and R$_3$ can be optionally substituted with one to three hydroxyls or halogens. In some embodiments, the alkyl groups and alkyl containing groups of R$_1$ and R$_3$ can be straight chain or branched alkyl groups, preferably having one to ten carbon atoms.

Also, included within the scope of the present invention are the non-toxic pharmaceutically acceptable salts of the compounds of the present invention. These salts can be prepared in situ during the final isolation and purification of the compounds or by separately reacting the purified compound in its free acid form with a suitable organic or inorganic base and isolating the salt thus formed. Examples of pharmaceutically acceptable salts include inorganic and organic base addition salts. These may include cations based on the alkali and alkali earth metals, such as sodium, lithium, potassium, calcium, magnesium, and the like, as well as nontoxic ammonium, quaternary ammonium and amine cations including, but not limited to ammonium, tetramethylammonium, tetraethylammonium, methylamine, dimethylamine, trimethylamine, ethylamine, N-methyl glucamine and the like.

Betulin and dihydrobetulin derivatives according to the present invention have been found to possess anti-retroviral, particularly anti-HIV, activity. The derivatives of the present invention are expected to have improved water solubility, and enhanced oral bioavailability. Also, due to the improved water solubility, it will be easier to formulate the analogs of the present invention into pharmaceutical preparations. Further, betulin and dihydrobetulin derivatives according to the present invention are expected to have improved biodistribution properties.

C3 acyl groups having dimethyl groups or oxygen at the C3' position are some of the most active compounds. This observation suggests that this type of acyl group might be important to the enhanced anti-HIV activity.

The invention is also directed to a method for treating a subject infected with HIV-1 by administering at least one of the above-noted betulin and dihydrobetulin derivatives, optionally in combination with any one or more of the known anti-AIDS therapeutics or an immunostimulant.

Other features, advantages, embodiments, aspects and objects of the present invention will be clear to those skilled in the areas of relevant art, based upon the description, teaching and guidance presented herein.

The analogs of the present invention have been discovered to have anti-retroviral activity, thus providing suitable compounds and compositions for treating retroviral infections, optionally with additional pharmaceutically active ingredients, such as anti-retroviral, anti-HIV, and/or immuno-stimulating compounds or anti-viral antibodies or fragments thereof.

By the term "anti-retroviral activity" or "anti-HIV activity" is intended the ability to inhibit at least one of:
(1) viral pro-DNA integration into host cell genome;
(2) retroviral attachment to cells;
(3) viral entry into cells;
(4) cellular metabolism which permits viral replication;
(5) inhibition of intercellular spread of the virus;
(6) synthesis and/or cellular expression of viral antigens;
(7) viral budding and maturation;
(8) activity of virus-coded enzymes (such as reverse transcriptase, integrase and proteases); and/or
(9) any known retroviral or HIV pathogenic actions, such as, for example, immunosuppression. Thus, any activity which tends to inhibit any of these mechanisms is "anti-retroviral activity" or "anti-HIV activity."

A betulin and dihydrobetulin derivative of the present invention can be used for treatment of retroviral (e.g., HIV) infection either alone, or in combination with other modes of therapy known in the art. Such modes of therapy can include chemotherapy with drugs, such as, but not limited to, at least one of AZT, 3TC, ddC, ddA, d4T, ddI, tenofovir, abacavir, nevirapine, delavirdine, efavirenz, saquinaviz, ritonavir, indinavir, nelfinavir, lopinavir, amprenavir, fosamprenavir, emtricitabine, atazanavir, or any other anti-retroviral drugs or antibodies in combination with each other, or associated with a biologically based therapeutic, such as, for example, gp-42-derived peptides enfuvirtide (Fuzeon®, Trimeris-Roche) and T-1249 (Trimeris), or soluble CD4, antibodies to CD4, and conjugates of CD4 or anti-CD4, or as additionally presented herein.

Because the betulin and dihydrobetulin derivatives of the present invention are relatively less or substantially non-toxic to normal cells, their utility is not limited to the treatment of established retroviral infections. For example, a betulin and dihydrobetulin derivative according to the present invention can be used in treating blood products, such as those maintained in blood banks. The nation's blood supply is currently tested for antibodies to HIV. However, the test is still imperfect and samples which yield negative tests can still contain HIV virus. Treating the blood and blood products with the betulin and dihydrobetulin derivatives of the present invention can add an extra margin of safety by killing any retrovirus that may have gone undetected.

In addition, betulin and dihydrobetulin derivatives of the present invention can be used as prophylactics to prevent transmission of HIV infection between individuals. For example, the derivatives can be administered orally or by injection to an HIV infected pregnant woman and/or fetus during pregnancy or immediately prior to, at, or subsequent to birth, to reduce the probability that the newborn infant becomes infected. Also, the derivatives can be administered vaginally immediately prior to childbirth to prevent infection of the infant during passage through the birth canal. Further, the derivatives of the present invention can be used during sexual intercourse to prevent transmission of HIV by applying a retroviral inhibiting effective amount of a topical composition including one or more compounds of Formula I to vaginal or other mucosa prior to sexual intercourse. For example, the derivatives of the present invention can be used to prevent transmission of HIV from an infected male to an uninfected female or vice versa.

Pharmaceutical Compositions

Pharmaceutical compositions of the present invention can comprise at least one of the betulin and dihydrobetulin derivatives. Pharmaceutical compositions according to the present invention can also further comprise other anti-viral agents such as, but not limited to, AZT (zidovudine, RETROVIR, GlaxoSmithKline), 3TC (lamivudine, EPIVIR®, GlaxoSmithKline), AZT+3TC, (COMBIVIR®, GlaxoSmithKline) AZT+3TC+abacvir (TRIZIVIR®, GlaxoSmithKline), ddI (didanosine, VIDEX®, Bristol-Myers Squibb), ddC (zalcitabine, HIVID®, Hoffmann-LaRoche), D4T (stavudine, ZERIT®, Bristol-Myers Squibb), abacavir (ZIAGEN®, GlaxoSmithKline), nevirapine (VIRAMUNE®, Boehringher Ingelheim), delavirdine (Pfizer), efavirenz (SUSTIVA®, DuPont Pharmaceuticals), tenofovir (VIREAD®, Gilead Sciences), saquinavir (INVIRASE®, FORTOVASE®, Hoffmann-La Roche), ritonavir (NORVIR®, Abbott Laboratories), indinavir (CRIXIVAN®, Merck and Company), nelfinavir (VIRACEPT®, Pfizer), amprenavir (AGENERASE®, GlaxoSmithKline), adefovir (PREVEON®, HEPSERA®, Gilead Sciences), atazanavir (REYATAZ®, Bristol-Myers Squibb), fosamprenavir (LEXIVA®, GlaxoSmithKline) and hydroxyurea (HYDREA®, Bristol-Meyers Squibb), or any other antiretroviral drugs or antibodies in combination with each other, or associated with a biologically based therapeutic, such as, for example, gp41-derived peptides enfuvirtide (FUZEON®, Roche and Trimeris) and T-1249, or soluble CD4, antibodies to CD4, and conjugates of CD4 or anti-CD4, or as additionally presented herein.

Additional suitable anti-viral agents for optimal use with a betulin and dihydrobetulin derivative of the present invention can include, but are not limited to, amphotericin B (FUNGIZONE®); Ampligen (mismatched RNA; Hemispherx Biopharma); BETASERON® (β-interferon, Chiron); butylated hydroxytoluene; Carrosyn (polymannoacetate); Castanospermine; Contracan (stearic acid derivative); Creme Pharmatex (containing benzalkonium chloride); 5-unsubstituted derivative of zidovudine; penciclovir (DENAVIR®, Novartis); famciclovir (FAMVIR®, Novartis); acyclovir (ZOVIRAX®, GlaxoSmithKline); cytofovir (VISTIDE®, Gilead); ganciclovir (CYTOVENE®, Hoffmann LaRoche); dextran sulfate; D-penicillamine (3-mercapto-D-valine); FOSCARNET® (trisodium phosphonoformate; AstraZeneca); fusidic acid; glycyrrhizin (a constituent of licorice root); HPA-23 (ammonium-21-tungsto-9-antimonate); ORNIDYL® (eflornithine, Aventis); nonoxynol; pentamidine isethionate (PENTAM-300); Peptide T (octapeptide sequence, Peninsula Laboratories); Phenytoin (Pfizer); INH or isoniazid; ribavirin (VIRAZOLE®, Valeant Pharmaceuticals); rifabutin, ansamycin (MYCOBUTIN®, Pfizer); CD4-IgG2 (Progenics Pharmaceuticals) or other CD4-containing or CD4-based molecules; Trimetrexate (Medimmune); suramin and analogues thereof (Bayer); and WELLFERON® (α-interferon, GlaxoSmithKline).

Pharmaceutical compositions of the present invention can also further comprise immunomodulators. Suitable immunomodulators for optional use with a betulin and dihydrobetulin derivative of the present invention in accordance with the present invention can include, but are not limited to: ABPP (Bropririmine); anti-human interferon-α-antibody; ascorbic acid and derivatives thereof; interferon-β; Ciamexon; cyclosporin; cimetidine; CL-246,738; colony stimulating factors, including GM-CSF; dinitrochlorobenzene; HE2000 (Hollis-Eden Pharmaceuticals); inteferon-γ; glucan; hyperimmune gamma-globulin (Bayer); immuthiol (sodium diethylthiocarbamate); interleukin-1 (Hoffmann-LaRoche, Amgen), interleukin-2 (IL-2) (Chiron); isoprinosine (inosine pranobex); Krestin; LC-9018 (Yakult); lentinan (Yamanouchi); LF-1695; methionine-enkephalin; Minophagen C; muramyl tripeptide, MTP-PE; naltrexone (Barr Laboratories); RNA immunomodulator; REMUNE® (Immune Response Corporation); RETICULOSE® (Advanced Viral Research Corporation); shosaikoto; ginseng; thymic humoral factor; Thymopentin; thymosin factor 5; thymosin 1 (ZADAXIN®, SciClone); thymostimulin; TNF (tumor necrosis factor, Genentech); and vitamin preparations.

The preferred animal subject of the present invention is a mammal. By the term "mammal" is meant an individual belonging to the class Mammalia. The invention is particularly useful in the treatment of human patients.

The term "treating" means the administering to subjects a betulin and dihydrobetulin derivative for purposes which can include prevention, amelioration, or cure of a retroviral-related pathology.

Medicaments are considered to be provided "in combination" with one another if they are provided to the patient concurrently or if the time between the administration of each medicament is such as to permit an overlap of biological activity.

In one preferred embodiment, at least one betulin or dihydrobetulin derivative comprises a single pharmaceutical composition.

Pharmaceutical compositions for administration according to the present invention can comprise at least one betulin or dihydrobetulin derivative according to the present invention in a pharmaceutically acceptable form optionally combined with a pharmaceutically acceptable carrier. These compositions can be administered by any means that achieve their intended purposes. Amounts and regimens for the administration of a betulin or dihydrobetulin derivative according to the present invention can be determined readily by those with ordinary skill in the clinical art of treating a retroviral pathology.

For example, administration can be by parenteral, such as subcutaneous, intravenous, intramuscular, intraperitoneal, transdermal, or buccal routes. Alternatively, or concurrently, administration can be by the oral route. The dosage administered depends upon the age, health and weight of the recipient, type of previous or concurrent treatment, if any, frequency of treatment, and the nature of the effect desired.

Compositions within the scope of this invention include all compositions comprising at least one betulin or dihydrobetulin derivative according to the present invention in an amount effective to achieve its intended purpose. While individual needs vary, determination of optimal ranges of effective amounts of each component is within the skill of the art. Typical dosages comprise about 0.1 to about 100 mg/kg body weight. The preferred dosages comprise about 0.5 to about 100 mg/kg body weight of the active ingredient. The more preferred dosages comprise about 1 to about 50 mg/kg body weight. The most preferred dosages comprise about 1 to about 20 mg/kg body weight.

Therapeutic administration can also include prior, concurrent, subsequent or adjunctive administration of at least one additional betulin or dihydrobetulin derivative according to the present invention or other therapeutic agent, such as an anti-viral or immune stimulating agent. In such an approach, the dosage of the second drug can preferably be the same as or different from the dosage of the first therapeutic agent. Preferably, the drugs are administered on alternate days in the recommended amounts of each drug.

Administration of a compound of the present invention can also optionally include previous, concurrent, subsequent or adjunctive therapy using immune system boosters or immunomodulators. In addition to the pharmacologically active compounds, a pharmaceutical composition of the present invention can also contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 1 to about 99 percent, preferably from about 20 to about 75 percent of active compound(s), together with the excipient.

Pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

Suitable excipients are, e.g., fillers such as saccharide, for example, lactose or sucrose, mannitol or sorbitol; cellulose preparations and/or calcium phosphates, such as tricalcium phosphate or calcium hydrogen phosphate; as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added such as the above-mentioned starches and also carboxymethyl starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions can be used, which can optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl cellulose phthalate are used. Dyestuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers can be added.

Possible pharmaceutical preparations which can be used rectally include, for example, suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions can be administered. Suitable lipophilic solvents or vehicles include fatty oils, such as sesame oil, or synthetic fatty acid esters, such as ethyl oleate or triglycerides. Aqueous injection suspensions that can contain substances which increase the viscosity of the suspension include, for example, sodium carboxymethyl cellulose, sorbitol, and/or dextran. Optionally, the suspension can also contain stabilizers.

A pharmaceutical formulation for systemic administration according to the invention can be formulated for enteral, parenteral or topical administration. Indeed, all three types of formulation can be used simultaneously to achieve systemic administration of the active ingredient.

Suitable formulations for oral administration include hard or soft gelatin capsules, dragees, pills, tablets, including coated tablets, elixirs, suspensions, syrups or inhalations and controlled release forms thereof.

Solid dosage forms in addition to those formulated for oral administration include rectal suppositories.

Prophylactic topical compositions for preventing HIV infection between individuals during childbirth or sexual intercourse include one or more compounds of Formula I and at least one pharmaceutically acceptable topical carrier or diluent. The topical composition can be, for example, in the form of an ointment, a cream, a gel, a lotion, a paste, a jelly, a spray, a foam, or a sponge. The dosage amount of a compound of Formula I in a prophylactic topical formulation is, in general, less than about 1,000 milligrams, preferably between about 0.01 to about 100 milligrams. The topical formulations can include other prophylactic ingredients. The carrier and diluents should be acceptable in the sense of being compatible with other ingredients of the formulation and not deleterious to the recipient.

Topical prophylactic formulations include those suitable for vaginal, rectal or topical administration. The formulations can, where appropriate, be conveniently presented in discrete dosage units, and can be prepared by any of the methods known in the art of pharmacy. All such methods include the step of bringing the active agent into association with liquid carriers, gels or finely divided solid carriers or both and then, if necessary, shaping the product into the desired formulation.

Prophylactic formulations suitable for vaginal administration can be presented as pessaries, tampons, creams, gels, pastes, jelly, foams, or sprays, or aqueous or oily suspensions, solutions or emulsions (liquid formulations) containing suitable carriers known in the art in addition to the active agent. Liquid formulations can contain conventional additives, such as, suspending agents, emulsifying agents, non-aqueous vehicles including edible oils, or preservatives. These formulations are useful to prevent both sexual transmission of HIV and infection of an infant during passage through the birth canal. In one example, the vaginal administration can take place prior to sexual intercourse, or immediately prior to childbirth.

Prophylactic formulations suitable for rectal or vaginal administration having a solid carrier are preferably represented as unit dose suppositories. Suitable carriers include cocoa butter and other materials commonly used in the art. Suppositories can be formed, for example, by mixing one or more compounds of Formula I with one or more softened or melted carriers followed by chilling and shaping in molds.

Prophylactic formulations according to the invention can also be in the form of drops formulated with an aqueous or non-aqueous base comprising one or more dispersing agents, solubilizing agents, or suspending agents. Liquid sprays can be delivered from pressurized packs.

Prophylactic formulations according to the invention can be adapted to give sustained delivery. Also, the prophylactic formulations can include other active agents, such as spermicidal agents, antimicrobial agents, and anti-viral agents.

The 3-O-acyl betulin and dihydrobetulin derivatives of the present invention can also be administered in the form of an implant when compounded with a biodegradable slow-release carrier. Alternatively, the betulin and dihydrobetulin derivatives of the present invention can be formulated as a transdermal patch for continuous release of the active ingredient.

Suitable formulations for topical administration include creams, gels, jellies, mucilages, pastes and ointments. Suitable injectable solutions include intravenous subcutaneous and intramuscular injectable solutions. Alternatively, the betulin and dihydrobetulin derivatives may be administered in the form of an infusion solution or as a nasal inhalation or spray.

The compounds of the present invention can be prepared using methods know to those skilled in the art. The exemplified 3-O-acyl betulin and dihydrobetulin derivatives of the present invention were prepared as shown in Scheme 1. Protection of the 28-hydroxyl group of betulin (1) with triphenylmethyl ether group yielded betulin 28-O-triphenylmethyl ether (2), whose solution in pyridine was further treated with an appropriate dicarboxylic acid in the presence of dimethylamino pyridine at reflux. Finally, the 28-protective group was removed by refluxing with pyridium p-toluenesulfonate in $CH_2Cl_2$-EtOH to give desired 3-O-acyl betulin derivatives. In some instances, the above reaction also yielded 3-O-acyl betulin ester derivatives in addition to the 3-O-acyl betulin derivatives. Conversion of the betulin derivatives to the dihydrobetulin derivatives was achieved by hydrogenation with hydrogen gas and a palladium catalyst.

SCHEME 1

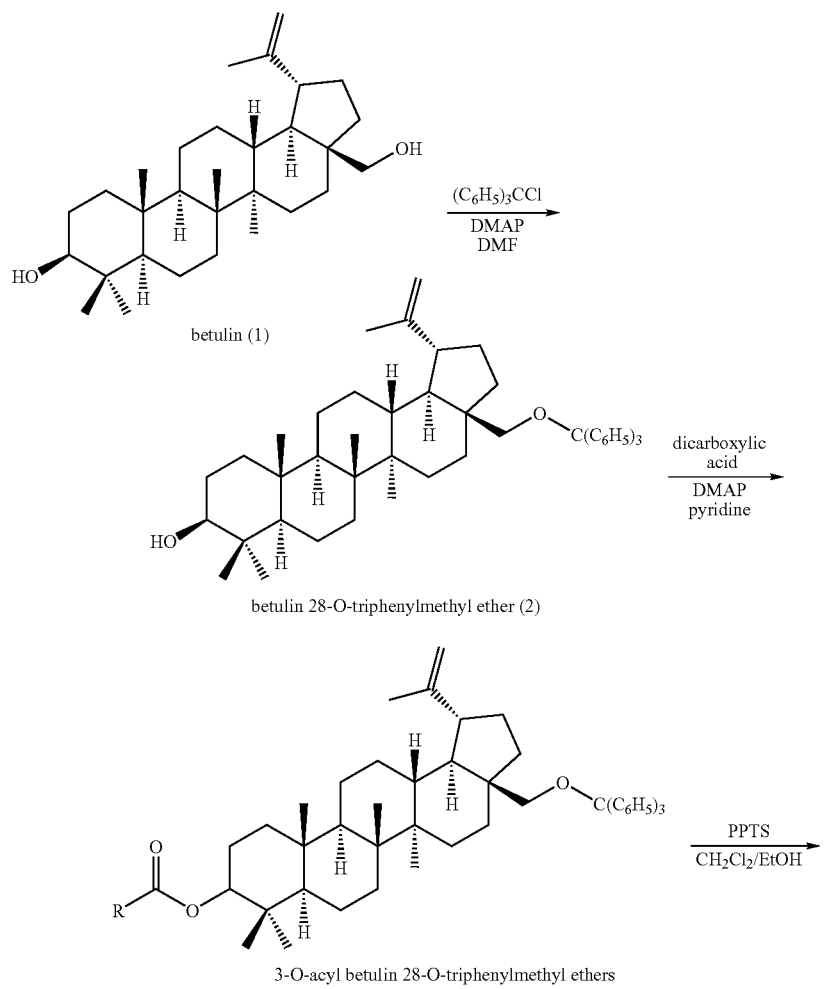

SCHEME 1-continued
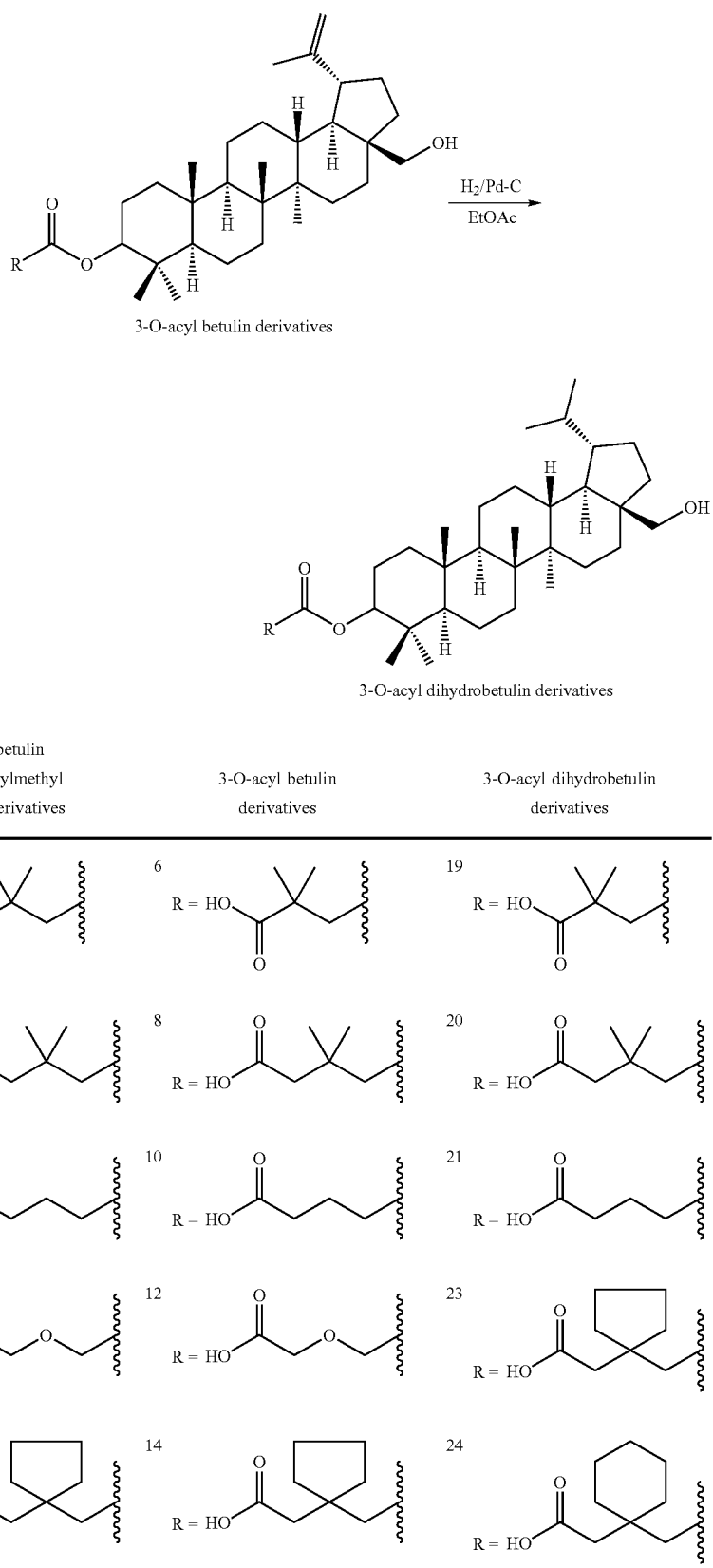

SCHEME 1-continued

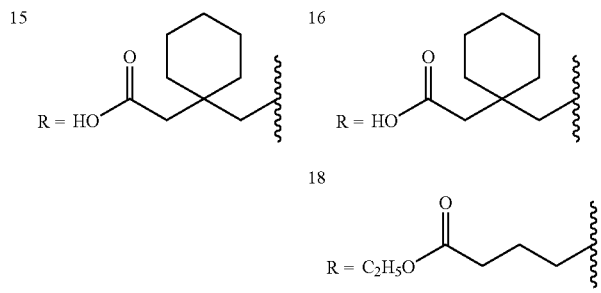

3-O-acyl betulin ester derivatives of the present invention can be prepared using methods know to those skilled in the art. For example, 18 was prepared as described above, by refluxing 3-O-glutaryl betulin 28-O-triphenylmethyl ether with pyridium p-toluenesulfonate in a 1:4 ratio of $CH_2Cl_2$: EtOH. Alternatively, 3-O-acyl betulin ester derivatives are prepared as exemplified in Scheme 2. 3-O-acyl betulin 28-O-triphenyl ether derivatives are treated with oxalyl chloride $(COCl)_2$, benzene and the desired alcohol (R-OH) to yield a 3-O-acyl betulin ester 28-O-triphenylmethyl ether. The 28-protective group is removed by refluxing with pyridium p-toluenesulfonate in a $CH_2Cl_2$:EtOH to yield the desired 3-O-acyl betulin ester derivatives.

The biological evaluation of HIV-1 inhibition was carried out as follows according to established protocols (Montefiori et al., *Clin Microbiol.* 26:231-235 (1988)). The human T-cell line, MT-2, was maintained in continuous culture with complete medium (RPMI 1640 with 10% fetal calf serum supplemented with L-glutamine at 5% $CO_2$ and 37° C.). Test samples were first dissolved in dimethyl sulfoxide at a concentration of 10 mg/ml to generate master stocks with dilutions made into tissue culture media to generate working stocks. The following drug concentrations were routinely used for screening: 100, 20, 4 and 0.8 μg/ml. For agents found to be active, additional dilutions were prepared for subsequent testing so that an accurate $EC_{50}$ value (defined

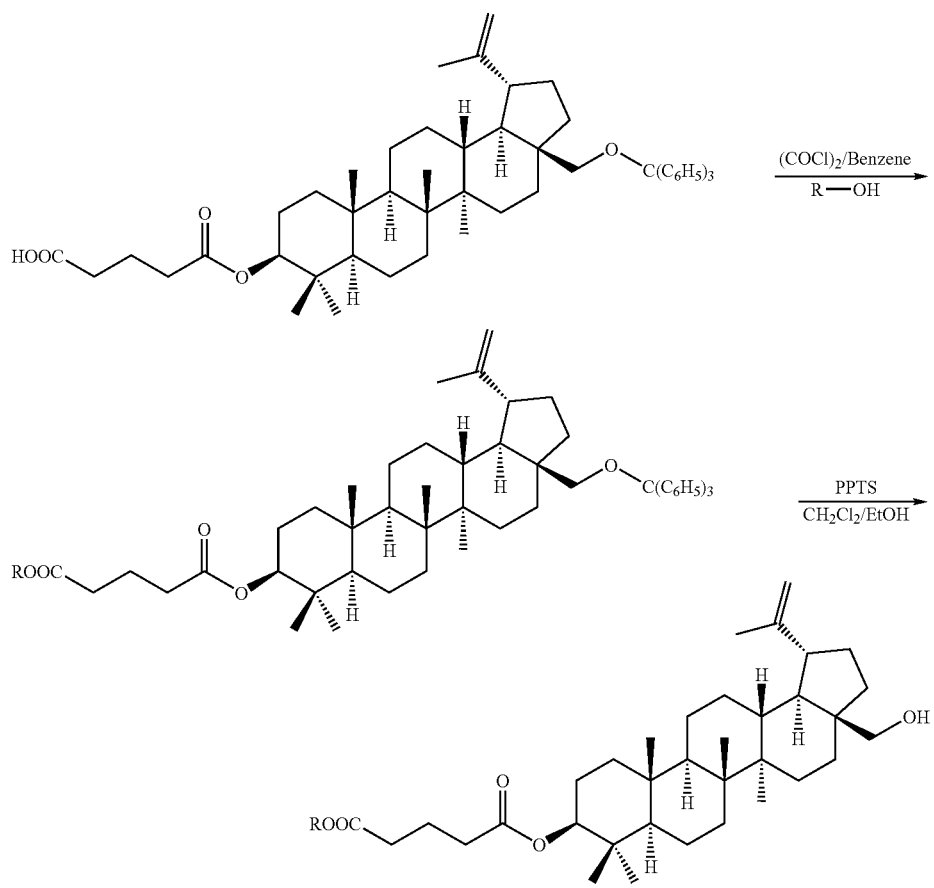

below) could be determined. Test samples were prepared and to each sample well was added 90 µl of media containing MT-2 cells at $3 \times 10^5$ cells/ml and 45 µl of virus inoculum (HIV-1 IIIIB isolate) at a concentration necessary to result in 80% killing of the cell targets at 5 days post-infection (PI). Control wells containing virus and cells only (no drug) and cells only (no virus or drug) were also prepared. A second set of samples were prepared identical to the first and were added to cells under identical conditions without virus (mock infection) for toxicity determinations ($IC_{50}$ defined below). In addition, AZT was also assayed during each experiment as a positive drug control. On day 5 PI, virus-induced cell killing was determined by measuring cell viability using the XTT method. Compound toxicity was determined by XTT using the mock-infected samples. If a test sample had suppressive capability and was not toxic, its effects were reported in the following terms: $IC_{50}$, the concentration of test sample which was toxic to 50% of the mock-infected MT-2 cells; $EC_{50}$, the concentration of the test sample that was able to suppress HIV replication by 50%; and the Therapeutic index (TI) the ratio of the $IC_{50}$ to $EC_{50}$.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

General Synthesis of Betulin Derivatives

Betulin 28-O-triphenylmethyl ether (2) was prepared by refluxing a solution of betulin (1) (10 g, 22.6 mmol), triphenylmethyl chloride (12.6 g, 45.2 mmol), and dimethylaminopyridine (3.3 g, 27.0 mmol) in DMF (75 mL) for 5 h with stirring. The reaction mixture was diluted with water, and extracted with $CHCl_3$. The organic layer was washed with water, dried over $Na_2SO_4$, and concentrated. Crystallization from EtOH yielded of betulin 28-O-triphenylmethyl ether (2) as colorless needles (11.4 g, 73.5% yield), mp 149-152 °C.; $[\alpha]_D^{18}$ −2.5° (c 0.8, $CHCl_3$); $^1$H-NMR ($CDCl_3$): 0.51 (3H, s, $CH_3$-26), 0.74 (3H, s, $CH_3$-24), 0.75 (3H, s, $CH_3$-25), 0.89 (3H, s, $CH_3$-27), 0.95 (3H, s, $CH_3$-23), 1.63 (3H, s, $CH_3$-29), 2.90, 3.13 (each 1H, d, J=9.0 Hz, $H_2$-28), 4.47 (1H, dd, J=5.0, 10.5 Hz, H-3), 4.51, 4.57 (each 1H, s, $H_2$-30), 7.20-7.50 (15H in total, m, aromatic-H).

3-O-acyl betulin 28-O-triphenylmethyl ethers were prepared by refluxing a solution of betulin 28-O-triphenylmethyl ether (1 equivalent mol), dimethylaminopyridine (1 equivalent mol), and appropriate dicarboxylic acid (2.5-4 equivalent mol) in anhydrous pyridine (5-25 mL) for overnight. The reaction mixture was diluted with ice-water, and extracted with $CHCl_3$. The organic layer was washed with water, dried over $Na_2SO_4$, and concentrated. The residue was chromatographed over silica gel column.

Compound 5 was prepared as above using solution of betulin 28-O-triphenylmethyl ether, dimethylaminopyridine, and dimethylsuccinic acid in anhydrous pyridine. The yield was 64%. A white amorphous powder; $[\alpha]_D^{18}$+2.3° (c 0.44, $CHCl_3$); $^1$H-NMR ($CDCl_3$): 0.50 (3H, s, $CH_3$-26), 0.76 (3H, s, $CH_3$-25), 0.79 (3H, s, $CH_3$-24), 0.81 (3H, s, $CH_3$-23), 0.88 (3H, s, $CH_3$-27), 1.28, 1.29 (each 3H, s, dimethylsuccinyl $CH_3$), 1.63 (3H, s, $CH_3$-29), 2.55, 2.66 (each 1H, d, J=15.9 Hz, dimethylsuccinyl $H_2$-2'), 2.90, 3.12 (each 1H, d, J=9.0 Hz, $H_2$-28), 3.16 (1H, dd, J=4.6, 11.0 Hz, H-3), 4.51, 4.56 (each 1H, s, $H_2$-30), 7.20-7.50 (15H in total, m, aromatic-H).

Compound 7: yield 82% (starting from 400 mg of 2): A white amorphous powder; $[\alpha]_D^{18}$+2.4° (c 0.84, $CHCl_3$); $^1$H-NMR ($CDCl_3$): 0.51 (3H, s, $CH_3$-26), 0.78 (3H, s, $CH_3$-25), 0.82 (3H, s, $CH_3$-24), 0.84 (3H, s, $CH_3$-23), 0.89 (3H, s, $CH_3$-27), 1.13 (6H, s, dimethylglutaryl $CH_3$P 1.63 (3H, s, $CH_3$-29), 2.38, 2.45 (each 1H, d, J=14.0 Hz, dimethylglutaryl $H_2$-2'), 2.45 (2H, s, dimethylglutaryl $H_2$-4'), 2.90, 3.13 (each 1H, d, J=9.0 Hz, $H_2$-28), 4.47 (1H, dd, J=5.0, 10.5 Hz, H-3), 4.51, 4.57 (each 1H, s, $H_2$-30), 7.20-7.50 (15H in total, m, aromatic-H).

Compound 9: yield 65% (starting from 285 mg of 2); A white amorphous powder; $[\alpha]_D^{18}$+3.0° (c 0.80, $CHCl_3$); $^1$H-NMR ($CDCl_3$): 0.51 (3H, s, $CH_3$-26), 0.78 (3H, s, $CH_3$-25), 0.82 (6H, s, $CH_3$-24 and -23), 0.89 (3H, s, $CH_3$-27), 1.63 (3H, s, $CH_3$-29), 1.95 (2H, quintet, J=7.3 Hz, glutaryl $H_2$-3'), 2.38, 2.41 (each 2H, t, J=7.3 Hz, glutaryl $H_2$-2' and -4'), 2.90, 3.13 (each 1H, d, J=9.0 Hz, $H_2$-28), 4.46 (1H, dd, J=5.0, 10.0 Hz, H-3), 4.51, 4.57 (each 1H, s, $H_2$-30), 7.20-7.50 (15H in total, m, aromatic-H).

Compound 11: yield 72% (starting from 278 mg of 2); A white amorphous powder; $[\alpha]_D^{18}$+2.7° (c 0.74, $CHCl_3$); $^1$H-NMR ($CDCl_3$): 0.50 (3H, s, $CH_3$-26), 0.73 (3H, s, $CH_3$-25), 0.76(3H, s, $CH_3$-24), 0.78 (3H, s, $CH_3$-23), 0.86 (3H, s, $CH_3$-27), 1.60 (3H, s, $CH_3$-29), 2.89, 3.12 (each 1H, d, J=9.0 Hz, $H_2$-28), 4.00, 4.16 (each 2H, br s, diglycoryl $H_2$-2' and -4'), 4.41 (1H, dd, J=5.0, 10.0 Hz, H-3), 4.47, 4.56 (each 1H, s, $H_2$-30), 7.20-7.50 (15H in total, m, aromatic-H).

3-O-acyl betulin derivatives were prepared by refluxing a solution of 3-O-acyl betulin 28-O-triphenylmethyl ether (1 equivalent mol) and pyridium p-toluenesulfonate (3-5 equivalent mol) in EtOH—$CH_2Cl_2$ for overnight. The reaction mixture was diluted with ice-water, and extracted with $CHCl_3$. The organic layer was washed with water, dried over $Na_2SO_4$, and concentrated. The residue was chromatographed over silica gel column or purified by HPLC.

Compound 6: yielded 70% (starting from 300 mg of 5); Colorless prisms (from EtOH); mp 269-271° C.; $[\alpha]_D^{18}$+21.0° (c 0.5, $CHCl_3$); $^1$H-NMR ($CDCl_3$): 0.81 (3H, s, $CH_3$-24), 0.84 (6H, s, $CH_3$-25 and -23), 0.94 (3H, s, $CH_3$-27), 1.08 (3H, s, $CH_3$-26), 1.28, 1.30 (each 3H, s, dimethylsuccinyl $CH_3$), 1.68 (3H, s, $CH_3$-29), 2.56, 2.67 (each 1H, d, J=15.9 Hz, dimethylsuccinyl $H_2$-2'), 3.34, 3.80 (each 1H, d, J=10.7 Hz, $H_2$-28), 4.49 (1H, dd, J=5.5, 11.0 Hz, H-3), 4.58, 4.68 (each 1H, br s, $H_2$-30).

Compound 8: yielded 51% (starting from 275 mg of 7); Colorless needles (from EtOH); mp 224-226° C.; $[\alpha]_D^{18}$+28.3° (c 0.46, $CHCl_3$); $^1$H-NMR ($CDCl_3$): 0.84 (3H, s, $CH_3$-24), 0.85 (3H, s, $CH_3$-25), 0.86 (3H, s, $CH_3$-23), 0.98 (3H, s, $CH_3$-27), 1.02 (3H, s, $CH_3$-26), 1.14 (6H, s, dimethylglutaryl $CH_3$), 1.68 (3H, s, $CH_3$-29), 2.40, 2.47 (each 1H, d, J=12.0 Hz, dimethylglutaryl $H_2$-2'), 2.46 (2H, s, dimethylglutaryl $H_2$-4'), 3.34, 3.80 (each 1H, d, J=10.5 Hz, $H_2$-28), 4.50 (1H, dd, J=5.0, 10.5 Hz, H-3), 4.58, 4.68 (each 1H, br s, $H_2$-30).

Compound 10: yield 73% (starting from 152 mg of 9); Colorless needles (from EtOH); mp 217-218° C.; $[\alpha]_D^{18}$+18.5° (c 0.38, $CHCl_3$); $^1$H-NMR ($CDCl_3$): 0.83 (3H, s, $CH_3$-24), 0.84 (3H, s, $CH_3$-23), 0.85 (3H, s, $CH_3$-25), 0.98 (3H, s, $CH_3$-27), 1.02 (3H, s, $CH_3$-26), 1.68 (3H, s, $CH_3$-29), 1.96 (2H, m, glutaryl $H_2$-3'), 2.39, 2.43 (each 2H, t, J=7.3 Hz, glutaryl $H_2$-2' and -4'), 3.34, 3.80 (each 1H, d, J=10.5 Hz, $H_2$-28), 4.49 (1H, dd, J=5.5, 10.5 Hz, H-3), 4.58, 4.68 (each 1H, br s, $H_2$-30).

Compound 12: yield 47% (starting from 150 mg of 11); A white amorphous powder; $[\alpha]_D^{18}$+22.2° (c 0.72, $CHCl_3$);

$^1$H-NMR (CDCl$_3$+CD$_3$OD): 0.84 (3H, s, CH$_3$-24), 0.85 (3H, s, CH$_3$-23), 0.86 (3H, s, CH$_3$-25), 0.98 (3H, s, CH$_3$-27), 1.03 (3H, s, CH$_3$-26), 1.68 (3H, s, CH$_3$-29), 3.31, 3.76 (each 1H, d, J=11.0 Hz, H$_2$-28), 4.04, 4.23 (each 2H, br s, diglycoryl H$_2$-2' and -4'), 4.56 (1H, dd, J=5.5, 10.5 Hz, H-3), 4.58, 4.68 (each 1H, br s, H$_2$-30).

Compound 14: yielded 43% (starting from 190 mg of 13); A white amorphous powder; [α]$_D$$^{18}$+14.8° (c 0.29, CHCl$_3$); $^1$H-NMR (CDCl$_3$): 0.84 (3H, s, CH$_3$-24), 0.85 (3H, s, CH$_3$-23), 0.85 (3H, s, CH$_3$-25), 0.98 (3H, s, CH$_3$-27), 1.02 (3H, s, CH$_3$-26), 1.69 (3H, s, CH$_3$-29), 2.51, 2.55 (each 1H, d, J=14.5 Hz, 3-O-acyl H-2' and 4'), 2.56 (2H, d, J=14.5 Hz, 3-O-acyl H'-2' and 4'), 3.34, 3.80 (each 1H, d, J=10.5 Hz, H$_2$-28), 4.50 (1H, dd, J=5, 10.5 Hz, H-3), 4.58, 4.68 (each 1H, br s, H$_2$-30).

Compound 16: yielded 48% (starting from 210 mg of 15); Colorless needles (from MeOH); mp 212-214° C.; [α]$_D$$^{18}$+17.6° (c 0.51, CHCl$_3$); $^1$H-NMR (CDCl$_3$): 0.85 (3H, s, CH$_3$-24), 0.85 (3H, s, CH$_3$-23), 0.86 (3H, s, CH$_3$-25), 0.98 (3H, s, CH$_3$-27), 1.03 (3H, s, CH$_3$-26), 1.68 (3H, s, CH$_3$-29), 2.50, 2.51 (each 1H, d, J=14.5 Hz, 3-O-acyl H-2' and 4'), 2.55 (2H, d, J=14.5 Hz, 3-O-acyl H'-2' and 4'), 3.34, 3.80 (each 1H, d, J=10.5 Hz, H$_2$-28), 4.51 (1H, dd, J=4.5, 11.3 Hz, H-3), 4.58, 4.68 (each 1H, br s, H$_2$-30).

EXAMPLE 2

General Synthesis of Dihydrobetulin Derivatives

3-O-acyl dihydrobetulin derivatives were prepared by treating a solution of 3-O-acyl betulin derivative (50 mg-103 mg) in ethyl acetate (EtOAc) with 10% palladium catalyst (Pd-C) (60-120 mg) under hydrogen gas overnight while stirring. The reaction mixture was filtered, and the filtrate was concentrated under reduced pressure. The product was purified by ODS column chromatography.

Compound 19: yielded 86% (starting from 103 mg of 6); Colorless needles (from MeOH); mp 273-274° C.; [α]$_D$$^{18}$-15.6° (c 0.5, pyridine); $^1$H-NMR (Pyridine-d$_5$): 0.84, 0.90 (each 3H, d, J=7.0 Hz, CH$_3$-29 and 30), 0.79, 0.95, 0.97, 0.97, 0.99 (each 3H, s, CH$_3$-23, 24, 25, 26, 27), 1.54 (6H, s, dimethylsuccinyl CH$_3$), 2.88, 2.95 (each 1H, d, J=15.5 Hz, dimethylsuccinyl H$_2$-2'), 3.59, 4.04 (each 1H, d, J=10.5 Hz, H$_2$-28), 4.76 (1H, dd, J=4.5, 11.8 Hz, H-3).

Compound 20: yielded 83% (starting from 80 mg of 8); Colorless needles (from MeOH); mp 224-225° C.; [α]$_D$$^{18}$-12.5° (c 0.4, pyridine); $^1$H-NMR (Pyridine-d$_5$) : 0.83, 0.90 (each 3H, d, J=7.0 Hz, CH$_3$-29 and 30), 0.81, 0.93, 0.95, 0.97, 1.00 (each 3H, s, CH$_3$-23, 24, 25, 26, 27), 1.37, 1.38 (each 3H, s, dimethylglutaryl CH$_3$), 2.75, 2.81 (each 1H, d, J=14 Hz, dimethylglutaryl H$_2$-2'), 2.69 (2H, s, dimethylglutaryl H$_2$-4'), 3.60, 4.05 (each 1H, d, J=11 Hz, H$_2$-28), 4.75 (1H, dd, J=4.5, 11.5 Hz, H-3).

Compound 21: yielded 74% (starting from 65 mg of 10); Colorless needles (from MeOH); mp 230-231° C.; [α]$_D$$^{18}$-6.6° (c 0.47, pyridine); $^1$H-NMR (Pyridine-d$_5$): 0.83, 0.89 (each 3H, d, J=6.7 Hz, CH$_3$-29 and 30), 0.81, 0.90, 0.91, 0.97, 1.01 (each 3H, s, CH$_3$-23, 24, 25, 26, 27), 2.23 (2H, m, glutaryl H$_2$-3'), 2.59-2.66 (4H, m, glutaryl H$_2$-2' and 4'), 3.60, 4.06 (each 1H, d, J=10.5 Hz, H$_2$-28), 4.74 (1H, dd, J=4.5, 11.5 Hz, H-3).

Compound 23: yielded 76% (starting from 56 mg of 14); Colorless needles (from MeOH); mp 240-242° C.; [α]$_D$$^{18}$-7.7° (c 0.39, pyridine); $^1$H-NMR (Pyridine-d$_5$): 0.83, 0.89 (each 3H, d, J=6.7 Hz, CH$_3$-29 and 30), 0.80, 0.95, 0.97, 0.97, 1.00 (each 3H, s, CH$_3$-23, 24, 25, 26, 27), 2.91, 2.95 (each 1H, d, J=14.5 Hz, 3-O-acyl H$_2$-2'), 2.92 (2H, s, 3-O-acyl H$_2$-4'), 3.60, 4.05 (each 1H, d, J=10.5 Hz, H$_2$-28), 4.77 (1H, dd, J=4, 11.8 Hz, H-3).

Compound 24: yielded 74% (starting from 50 mg of 16); Colorless needles (from MeOH); mp 243-244° C.; [α]$_D$$^{18}$-7.2° (c 0.5, pyridine); $^1$H-NMR (Pyridine-d$_5$): 0.83, 0.89 (each 3H, d, J=6.7 Hz, CH$_3$-29 and 30), 0.81, 0.95, 0.97, 0.98, 1.00 (each 3H, s, CH$_3$-23, 24, 25, 26, 27), 2.91, 2.97 (each 1H, d, J=14 Hz, 3-O-acyl H$_2$-2'), 2.92 (2H, s, 3-O-acyl H$_2$-4'), 3.59, 4.05 (each 1H, d, J=10.8 Hz, H$_2$-28), 4.77 (1H, dd, J=4.5, 11.5 Hz, H-3).

EXAMPLE 3

Synthesis of 3-O-Acyl Betulin Ester Derivatives

3-O-glutaryl betulin 28-O-triphenylmethyl ether (9) (300 mg) was treated with pyridium p-toluenesulfonate (310 mg) in CH$_2$Cl$_2$-EtOH (1:4, 7 mL) at reflux for overnight. The reaction mixture was diluted with CHCl$_3$ and washed with H$_2$O. The organic layer was dried over Na$_2$SO$_4$ and concentrated. The products was separated by ODS chromatography to give 3-O-glutaryl betulin (10) (60 mg) and 3-O-glutaryl betulin ethyl ester (18) (145 mg).

Compound 18: A white amorphous powder; [α]$_D$$^{18}$+22.8° (c 0.79, CHCl$_3$); $^1$H-NMR (Pyridine-d$_5$): 0.78, 0.88, 0.89, 0.96, 1.28 (each 3H, s, CH$_3$-23, 24, 25, 26, 27), 1.12 (3H, t, J=7 Hz, CH$_3$-CH$_2$), 1.76 (3H, s, CH$_3$-30), 2.08 (1H, m, glutaryl H$_2$-3'), 2.48 (2H, t, J=7.3 Hz, glutaryl H$_2$-2'), 2.48-2.64 (2H, m, glutaryl H$_2$-4'), 3.66, 4.07 (each 1H, d, J=1 1 Hz, H$_2$-28), 4.11 (2H, q, J=7 Hz, CH$_2$-CH$_3$), 4.71 (1H, dd, J=4.5, 11.8 Hz, H-3), 4.75, 4.88 (each 1H, br s, H$_2$-30).

EXAMPLE 4

Pharmacological Activity

Compounds of the present invention were assayed for anti-HIV activity according to the following assay procedures. The T cell line, H9, and the promonocytic cell line, U937, were maintained separately in continuous culture with complete medium (RPMI 1640 with 10% fetal calf serum) at 5% CO$_2$ and 37° C. The cell lines were used in experiments only when in the logarithmic phase of growth, whereas uninfected peripheral blood mononuclear cells (PB-MCs) were first stimulated with PHA (1 μg/mL) for three days. All cell targets were incubated with HIV-1 (IIIB isolate, 1×10$^6$ TCID$_{50}$/mL) for one hour at 37° C. and 5% CO$_2$. The cell lines and PBMCs were washed thoroughly to remove unadsorbed virions and resuspended at 4×10$^5$ cells/mL in complete medium or complete medium with 10% v/v interleukin 2 (IL-2), respectively. 100 μL aliquots were placed into wells of 96-well tissue culture plates containing an equal volume of test compounds (diluted in the appropriate culture medium). The toxicity of each compound was assessed by determining the number of compound-exposed uninfected cells that remained after five days at 37° C. and 5% CO$_2$. A p24 antigen ELISA assay was used to determine the level of virus released in the medium of the HIV-infected cultures. The p24 antigen assay used a HIV-1 anti-p24 specific monoclonal antibody as the capture antibody coated onto 96-well plates. Following a sample incubation period, rabbit serum containing antibodies for HIV-1 p24 was used to tag any p24 captured onto the microtiter well surface. Peroxidase conjugated goat anti-rabbit serum was then used to tag HIV-1 p24 specific rabbit antibodies that had complexed with captured p24. The presence of p24 in test samples was then revealed by addition of substrate. The cutoff for the p24 ELISA assay was 12.5 pg/mL. p24 in the culture medium was quantitated against a standard curve containing known amounts of p24. The effective ($EC_{50}$) and inhibitory ($IC_{50}$) concentrations for anti-HIV activity and cytotoxicity, respectively, were determined.

TABLE 1

Anti-HIV Activities of Betulin and Related Derivatives

| Compound | Anti-HIV* Activity $EC_{50}$ (µM) | Cytotoxicity* $IC_{50}$ (µM) | Therapeutic Index (=$IC_{50}/EC_{50}$) |
|---|---|---|---|
| 6 | 0.0056 | 33.46 | 5975 |
| 8 | 0.0044 | 28.90 | 6568 |
| 10 | 0.0662 | 44.36 | 670 |
| 12 | 0.0246 | >44.75 | >1819 |
| 14 | 0.0464 | 25.12 | 824 |
| 16 | 0.147 | 24.68 | 384 |
| 18 | 0.0169 | 36.42 | 55340 |
| 19 | 0.0017 | 26.99 | 16160 |
| 20 | 0.0013 | 25.69 | 19530 |
| 21 | $2 \times 10^{-5}$ | 23.59 | $1.12 \times 10^6$ |
| 23 | 0.0151 | 25.11 | 1818 |

*all the data represented as an average of at least two experiments.

Those skilled in the art will recognize that while specific embodiments have been illustrated and described, various modifications and changes may be made without departing from the spirit and scope of the invention.

Other embodiments of the invention will be apparent to those skilled in the art from consideration of the specification and practice of the invention disclosed wherein. It is intended that the specification and examples be considered as exemplary only, with a true scope and spirit of the invention being indicated by the following claims. All publications, patent applications and patents cited herein are fully incorporated by reference.

What is claimed is:

1. A compound of Formula I:

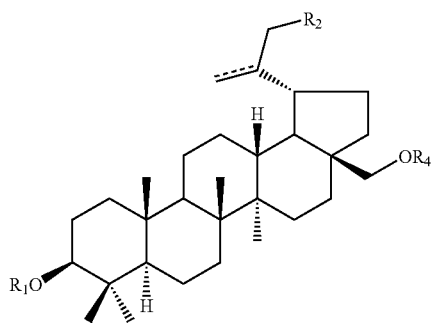

I or a pharmaceutically acceptable salt thereof, wherein: $R_1$ is one of:
   (i) —C(O)CH$_2$CR'R"(CH$_2$)$_b$COOH,
   (ii) —C(O)(CH$_2$)$_d$CR'R"(CH$_2$)$_b$COOR$_5$, or
   (iii) —C(O)CH$_2$O(CH$_2$)$_a$COOH
wherein when $R_1$ is (i), R' and R" are each $C_1$-$C_4$ alkyl, or R' and R" are taken together to form a di-, tri-, tetra-, penta-, hexa-, or heptamethylene linkage, and
when $R_1$ is (ii), R' and R" are each $C_1$-$C_4$ alkyl, or R' is hydrogen and R" is $C_1$-$C_4$ alkyl, or R' and R" are taken together to form a di-, tri-, tetra-, penta-, hexa-, or heptamethylene linkage;

$R_5$ is $C_1$-$C_6$ alkyl or $C_1$-$C_6$ carboxyalkyl,
a is from zero to twelve,
b is from zero to twelve,
d is from zero to twelve;
$R_2$ is hydrogen, halogen, hydroxyl or —OR$_3$;
$R_3$ is $C_2$-$C_{20}$ substituted or unsubstituted carboxyacyl; and
$R_4$ is hydrogen or C(C$_6$H$_5$)$_3$;
wherein the dashed line represents an optional double bond between C20 and C29.

2. A compound according to claim 1, wherein $R_2$ is hydrogen.

3. A compound according to claim 1, wherein $R_2$ is halogen or —OR$_3$, where $R_3$ is hydrogen or $C_2$-$C_{20}$ substituted or unsubstituted carboxyacyl.

4. A compound according to claim 1, wherein $R_1$ has the formula:

—C(O)CH$_2$CR'R"(CH$_2$)$_b$COOH where R' and R" are each $C_1$-$C_4$ alkyl, or R' and R" are taken together to form a di-, tri, tetra-, penta-, hexa-, or heptamethylene linkage, and b is from zero to twelve.

5. A compound according to claim 4, wherein b is zero to 4.

6. A compound according to claim 5, wherein R' and R" are each methyl, and b is zero or 1.

7. A compound according to claim 1, wherein $R_1$ has the formula:

—C(O)CH$_2$O(CH$_2$)$_a$COOH, where a is from zero to twelve.

8. A compound according to claim 1, wherein $R_1$ has the formula:

—C(O)(CH$_2$)$_d$CR'R"(CH$_2$)$_b$COOR$_5$, wherein;
   R' and R" are each $C_1$-$C_4$ alkyl, or R' is hydrogen and R" is $C_1$-$C_4$ alkyl, or R' and R" are taken together to form a di-, tri-, tetra-, penta-, hexa-, or heptamethylene linkage;
   d is from zero to twelve;
   b is from zero to twelve; and
   $R_5$ is $C_1$-$C_6$ alkyl or $C_1$-$C_6$ carboxyalkyl.

9. A compound according to claim 8, wherein $R_5$ is ethyl.

10. A compound according to claim 1, wherein $R_2$ is hydrogen and a double bond exists between C20 and C29.

11. A compound according to claim 1, wherein $R_2$ is:

—O—C(O)CH$_2$CR'R"(CH$_2$)$_b$COOH, where R' and R" are each methyl, and b is zero or one.

12. A compound according to claim 1, wherein:
   $R_1$ is one of:

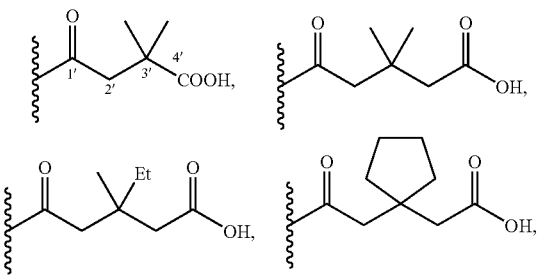

-continued

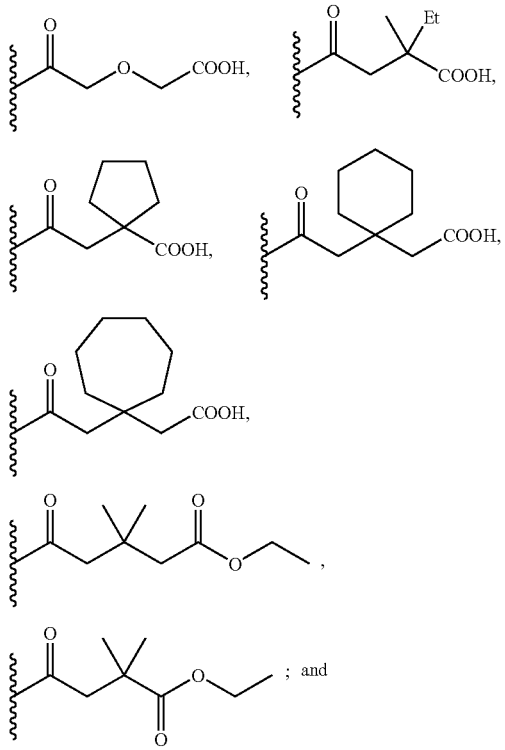

$R_2$ is hydrogen or hydroxyl.

13. A compound according to claim 1, wherein:
$R_1$ is

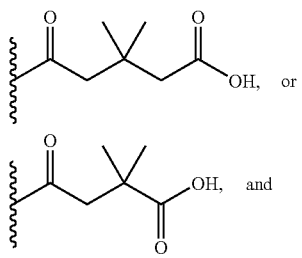

$R_2$ is hydrogen.

14. A compound according to claim 1, wherein:
$R_1$ is

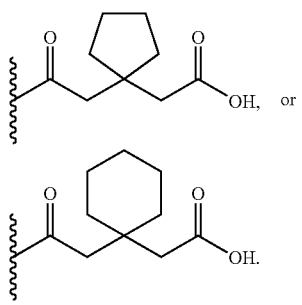

15. A compound according to claim 1, wherein:
$R_1$ is

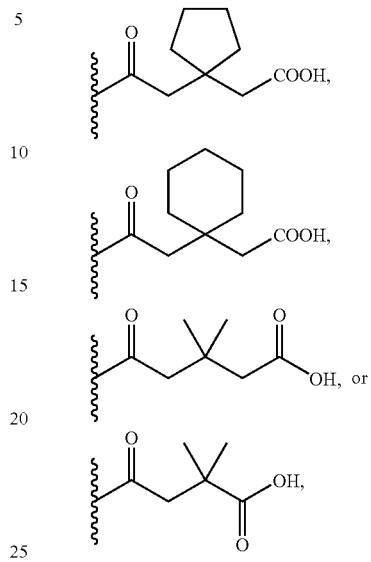

$R_2$ is H; and
a double bond exists between C20 and C29.

16. A compound according to claim 1, wherein:
$R_1$ is

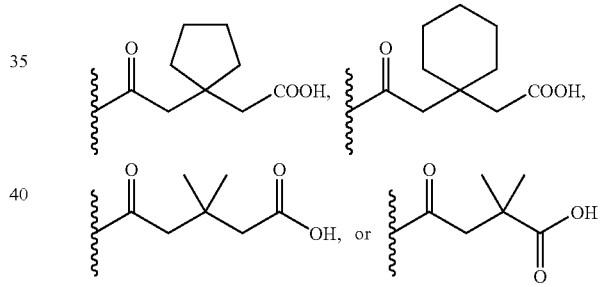

$R_2$ is H; and
a single bond exists between C20 and C29.

17. A compound according to claim 1, wherein $R_1$ and $R_3$ can be optionally substituted with one to three hydroxyl or halogen.

18. A pharmaceutical composition comprising one or more compounds according to claim 1, or a pharmaceutically acceptable salt, ester, or prodrug thereof, and ester, salt, ether, sulfate, or glucuronide thereof, and a pharmaceutically acceptable carrier.

19. A pharmaceutical composition according to claim 18, further comprising one or more drugs selected from an anti-viral agent or an immunostimulating agent.

20. A pharmaceutical composition according to claim 19, wherein said anti-viral agent is selected from the group consisting of one or more of zidovudine, lamivudine, zalcitabine, stavudine, didanosine, tenofovir, abacavir, nevirapine, delavirdine, emtricitabine, efavirenz, saquinavir, ritonavir, indinavir, nelfinavir, lopinavir, amprenavir, atazanavir, enfuvirtide, hydroxyurea, interleukin-2, gamma globulin, amantadine, guanidine hydroxybenzimidazole, interferon-α, interferon-β, interferon-γ, a thiosemicarbazone, methisazone, rifampin, ribavirin, a pyrimidine analog, a purine analog, foscarnet, phosphonoacetic acid, acyclovir, a dideoxynucleoside, and gancyclovir.

21. A pharmaceutical composition comprising one or more compounds according to claim 4, or a pharmaceutically acceptable salt, ester, or prodrug thereof, ester, salt, ether, sulfate, or glucuronide thereof, and a pharmaceutically acceptable carrier.

22. A pharmaceutical composition according to claim 21, further comprising a drug selected from an anti-viral agent or an immunostimulating agent.

23. A pharmaceutical composition according to claim 22, wherein said anti-viral agent is selected from the group consisting of one or more of zidovudine, lamivudine, zalcitabine, stavudine, didanosine, tenofovir, abacavir, nevirapine, delavirdine, emtricitabine, efavirenz, saquinavir, ritonavir, indinavir, nelfinavir, lopinavir, amprenavir, fosamprenavir, atazanavir, enfuvirtide, hydroxyurea, interleukin-2, gamma globulin, amantadine, guanidine hydroxybenzimidazole, interferon-α, interferon-β, interferon-γ, a thiosemicarbazone, methisazone, rifampin, ribavirin, a pyrimidine analog, a purine analog, foscarnet, phosphonoacetic acid, acyclovir, a dideoxynucleoside, and ganciclovir.

* * * * *